US010873710B2

(12) United States Patent
Wagner

(10) Patent No.: US 10,873,710 B2
(45) Date of Patent: Dec. 22, 2020

(54) IR/NIR IMAGING WITH DISCRETE SCALE COMPARATOR OBJECTS

(71) Applicant: CHRISTIE MEDICAL HOLDINGS, INC., Lake Mary, FL (US)

(72) Inventor: Robert Benjamin Wagner, Kitchener (CA)

(73) Assignee: CHRISTIE MEDICAL HOLDINGS, INC., Lake Mary, FL (US)

( * ) Notice: Subject to any disclaimer, the term of this patent is extended or adjusted under 35 U.S.C. 154(b) by 67 days.

(21) Appl. No.: 16/175,919

(22) Filed: Oct. 31, 2018

(65) Prior Publication Data

US 2020/0099869 A1 Mar. 26, 2020

Related U.S. Application Data

(60) Provisional application No. 62/735,456, filed on Sep. 24, 2018.

(51) Int. Cl.
*A61B 5/00* (2006.01)
*H04N 5/33* (2006.01)
*A61B 5/02* (2006.01)
*H04N 5/445* (2011.01)
*H04N 9/43* (2006.01)
*H04N 9/31* (2006.01)

(52) U.S. Cl.
CPC ............ *H04N 5/33* (2013.01); *A61B 5/0077* (2013.01); *A61B 5/02007* (2013.01); *H04N 5/445* (2013.01); *H04N 9/43* (2013.01); *H04N 9/31* (2013.01)

(58) Field of Classification Search
CPC ................... A61B 5/02154; A61B 5/02156
See application file for complete search history.

(56) References Cited

U.S. PATENT DOCUMENTS

2001/0026363 A1* 10/2001 Brinkman ............... G01B 11/26
356/138
2002/0062061 A1* 5/2002 Kaneko ................... A61B 1/045
600/118
2002/0128557 A1* 9/2002 Hohla ................. G01N 21/6486
600/476

(Continued)

FOREIGN PATENT DOCUMENTS

| EP | 2641538 A1 | 9/2013 |
| EP | 2689723 A2 | 1/2014 |
| WO | 97/31570 | 9/1997 |

OTHER PUBLICATIONS

EPO, Extended European Search Report, dated May 21, 2019, re European Patent Application No. 18203316.7.

(Continued)

*Primary Examiner* — Pankaj Kumar
*Assistant Examiner* — Timothy R Newlin
(74) *Attorney, Agent, or Firm* — Perry + Currier Inc.

(57) ABSTRACT

An imager captures images of a living subject including a near-infrared image, an infrared image, or both. A processor is connected to the imager and an output device. The processor is configured to generate output images of vasculature of the living subject from the images captured by the imager, include in the output images a range of discrete scale comparator objects of different sizes, and provide the output images to the output device for display to a user.

20 Claims, 6 Drawing Sheets

(56) References Cited

U.S. PATENT DOCUMENTS

| | | | | |
|---|---|---|---|---|
| 2003/0208123 | A1* | 11/2003 | Panescu | A61B 8/483 |
| | | | | 600/431 |
| 2004/0135823 | A1* | 7/2004 | Wingett | G06F 3/0236 |
| | | | | 715/856 |
| 2006/0167386 | A1* | 7/2006 | Drake | A61B 5/02007 |
| | | | | 600/587 |
| 2009/0036776 | A1* | 2/2009 | Masuda | A61B 8/4218 |
| | | | | 600/449 |
| 2010/0168642 | A1* | 7/2010 | Appling | A61M 1/3661 |
| | | | | 604/6.16 |
| 2011/0235878 | A1* | 9/2011 | Nakayama | G06T 7/12 |
| | | | | 382/128 |
| 2013/0253301 | A1* | 9/2013 | Park | A61B 6/5217 |
| | | | | 600/407 |
| 2014/0188133 | A1* | 7/2014 | Misener | A61M 25/0102 |
| | | | | 606/130 |
| 2014/0210972 | A1* | 7/2014 | On | H04N 5/2256 |
| | | | | 348/65 |
| 2014/0221874 | A1* | 8/2014 | Park | A61B 90/39 |
| | | | | 600/587 |
| 2015/0029461 | A1* | 1/2015 | Hoshino | A61B 3/0025 |
| | | | | 351/206 |
| 2015/0141814 | A1* | 5/2015 | Lee | A61B 6/037 |
| | | | | 600/425 |
| 2015/0209113 | A1 | 7/2015 | Burkholz et al. | |
| 2015/0257735 | A1 | 9/2015 | Ball et al. | |
| 2017/0120080 | A1* | 5/2017 | Phillips | A61B 8/445 |
| 2017/0303847 | A1 | 10/2017 | Drucker | |
| 2018/0015256 | A1* | 1/2018 | Southard | H03H 9/13 |
| 2018/0042522 | A1* | 2/2018 | Subramanian | H01G 4/1209 |
| 2018/0098820 | A1* | 4/2018 | Park | A61B 6/12 |
| 2018/0132797 | A1* | 5/2018 | Draeger | A61B 5/1072 |
| 2019/0117179 | A1* | 4/2019 | Goyal | A61B 6/486 |

OTHER PUBLICATIONS

Rivera, A.M., et al. "Matching the peripheral intravenous catheter to the individual patient." Acta Ansthesiologica Belgica 58.1 (2006): 19.

Pedagogy, Inc., "Peripheral IV Catheter Chart", Jul. 27, 2016, URL: https://www.pedagogyeducation.com/PedagogyEducation/media/Resources/Posters/Peripheral-IV-Catheters-Chart.pdf.

* cited by examiner

IR/NIR IMAGING WITH DISCRETE SCALE COMPARATOR OBJECTS

FIELD

This disclosure relates to computer imaging, such as vascular imaging.

BACKGROUND

Vascular imaging is a useful tool that helps clinicians visualize a subject's vasculature. Vascular imaging devices may be used to assist in insertion of a catheter into a patient's blood vessel. However, vascular imaging is an imperfect approximation of a patient's true vasculature and thus may not sufficiently help to prevent errors in catheter selection.

SUMMARY

According to an aspect of this disclosure, a device includes an imager to capture images of a living subject including a near-infrared image, an infrared image, or both. The device further includes an output device and a processor connected to the imager and the output device. The processor is configured to generate output images of vasculature of the living subject from the images captured by the imager, include in the output images a range of discrete scale comparator objects of different sizes, and provide the output images to the output device for display to a user.

According to another aspect of this disclosure, method to assist insertion of a catheter includes capturing images of a living subject including a near-infrared image, an infrared image, or both. The method further includes generating output images of vasculature of the living subject from the images captured by the imager, including in the output images a range of discrete scale comparator objects of different sizes, and providing the output images to the output device for display to a user.

According to another aspect of this disclosure, a device includes an imager to capture images of a living subject including a near-infrared image, an infrared image, or both. The device further includes an output device and a processor connected to the imager and the output device. The processor is configured to dynamically generate output images of vasculature of the living subject from the images captured by the imager. The vasculature is rendered in false color. The processor is further configured to include in the output images a relatively static range of discrete scale comparator objects of different sizes that are relative to an apparent size of the vasculature. The range of discrete scale comparator objects represents standard gauge sizes and standard colors of peripheral intravenous catheters. The processor is further configured to render in the output images the standard colors of the peripheral intravenous catheters in true color and provide the output images to the output device for display to a user.

DETAILED DESCRIPTION

Various techniques for vascular imaging use the principle that photon scattering in soft tissue is dependent on photon wavelength and tissue composition, as is known from the Kubelka-Munk theory of reflectance. Projecting an incident beam of diffuse light on tissue results partly in backscattered light, which is detectable at the surface of the tissue, and forward-scattered light that travels through the tissue. The forward scattered light interacts with scattering sites within the tissue and loses its intensity due to elastic and inelastic scattering phenomena. The inelastic phenomenon is also known as absorption. The intensity of the backscattered light is dependent on the type of tissue at the point of observation. Infrared (IR) light, near-infrared (NIR) light, or a combination of such, hereinafter referred to as IR/NIR light/illumination, may be used to illuminate a living subject's soft tissue for vascular imaging. Wavelengths in the range of 650-1100 nm may be used.

Figure 1:
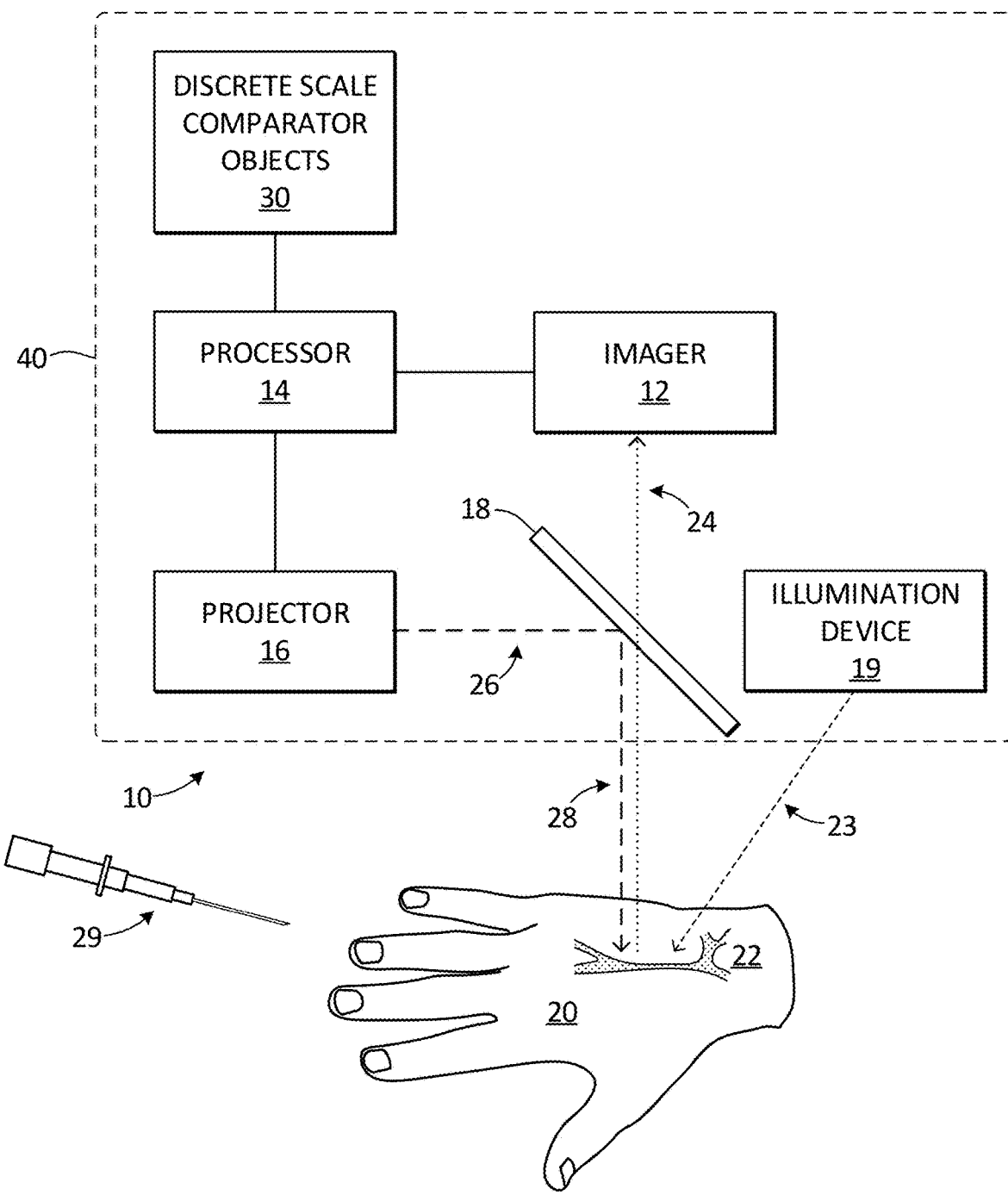
FIG. 1 is a block diagram of a device for vascular imaging with scale comparator objects.

FIG. 1 illustrates an imaging device 10 according to an embodiment of the present invention. The imaging device 10 will be described in the context of IR/NIR imaging for medical use, however, it should be understood that the device 10 may find use in other fields.

The imaging device 10 includes an imager 12, a processor 14, an output device 16, beam splitter 18, and an illumination device 19. The output device 16, in this embodiment, is a projector. The processor 14 is connected to the imager 12 and the projector 16 and may be connected to the illumination device 19. The processor 14 is configured to process image information collected by the imager 12 and output image information to the projector 16.

The illumination device 19 may include an IR/NIR light emitting diode (LED). The illumination device 19 illuminates a target object, such as a target tissue 20 (e.g., a region of a subject's skin surface), with IR/NIR illumination.

The imager 12 captures reflected IR/NIR light via the beam splitter 18. The imager 12 may include a camera.

The processor 14 may include a digital signal processor (DSP), central processing unit (CPU), a microcontroller, a microprocessor, a processing core, a field-programmable gate array (FPGA), or a similar device capable of executing instructions. The processor 14 may cooperate with a non-transitory machine-readable medium that may be an electronic, magnetic, optical, or other physical storage device capable of encoding executable instructions. The machine-readable medium may include, for example, random access memory (RAM), read-only memory (ROM), electrically-erasable programmable read-only memory (EEPROM), flash memory, a logic gate array, a storage drive, an optical disc, or similar. The functionality described herein may be encoded at a non-transitory machine-readable medium as processor-executable instructions.

The processor 14 processes captured IR/NIR images of the target tissue 20 to generate false-color images of vasculature for the projector 16 to output. The projector 16 projects the false-color images of vasculature through the beam splitter 18 and onto the target tissue 20.

As such, the imaging device 10 is capable of performing vasculature imaging and projecting a false-color images 22 of the vasculature directly back onto the target tissue 20, dynamically in real time or near real time, so that an operator of the device 10 may view images 22 of the vasculature in context of the actual target tissue 20. In other embodiments, the output device 16 may be a screen or similar device that displays an image of the target tissue 20 combined with images of the vasculature 22. An example projection or display frame rate is 60 frames per second (FPS). The projection or display frame rate may be faster than an image capture frame rate to avoid loss of data. An example imaging frame rate is 30 FPS, or slightly higher, to provide near real time imaging while providing sufficient processing time for each image frame.

In this embodiment, IR/NIR light is shone onto the target tissue 20 via an illumination path 23 and is reflected by the tissue 20 to the imager 12 along an imaging optical path 24. In other embodiments, IR/NIR light is emitted towards the target tissue 20 along a different path, such as a path parallel or coincident with the imaging optical path 24.

The projector 16 is arranged to project images along a projecting optical path 26 and onto the target tissue 20. The projector 16 can be any suitable kind of projector 16 and may include an I/O interface for connecting to the processor 14, a controller for controlling operations of the projector 16, a projection light source (e.g., a lamp, laser, LED), and an imaging device, such as LCD light valves, a digital micro-mirror device (DMD), or similar.

The projecting optical path 26 extends from the projector 16 to the target tissue 20 via the beam splitter 18. The projecting optical path 26 at least partially overlaps the imaging optical path 24, as shown by common optical path 28. In this embodiment, the optical paths 24, 26 overlap between the beam splitter 18 and the target tissue 20 along the common optical path 28, and do not overlap between the beam splitter 18 and the imager 12 or projector 16. The common optical path 28 is advantageous in that vascular imagery 22 can be projected directly onto the target tissue 20 being examined, at true or nearly true scale, and will remain at a consistent scale irrespective of a distance between the device 10 and the target tissue 20, over an acceptable range of distances that may be limited by the capabilities of the optics used. In this embodiment, the beam splitter 18 is configured to reflect the projecting optical path 26 and allow the imaging optical path 24 to pass through. In other embodiments, the beam splitter 18 is configured to reflect the imaging optical path 24 and allow the projecting optical path 26 to pass through, with the positions of the imager 12 and the projector 16 being reversed.

The imaging device 10 may be used by a clinician or other user to facilitate the insertion a catheter 29 into a blood vessel of the subject. For example, a nurse may use the imaging device to locate a suitable vein to insert a peripheral intravenous (IV) catheter.

The imaging device 10 may include a range of discrete scale comparator objects 30 of different sizes to assist the user of the device 10 in selecting a suitably sized peripheral IV catheter. The range of discrete scale comparator objects 30 includes at least two objects of differing size. The objects 30 may be stored as graphical objects, such as regions in an overlay image, in a memory that is accessible to the processor 14. The range of discrete scale comparator objects 30 may have sizes that are representative of the different sizes of peripheral IV catheter available.

Figure 2:
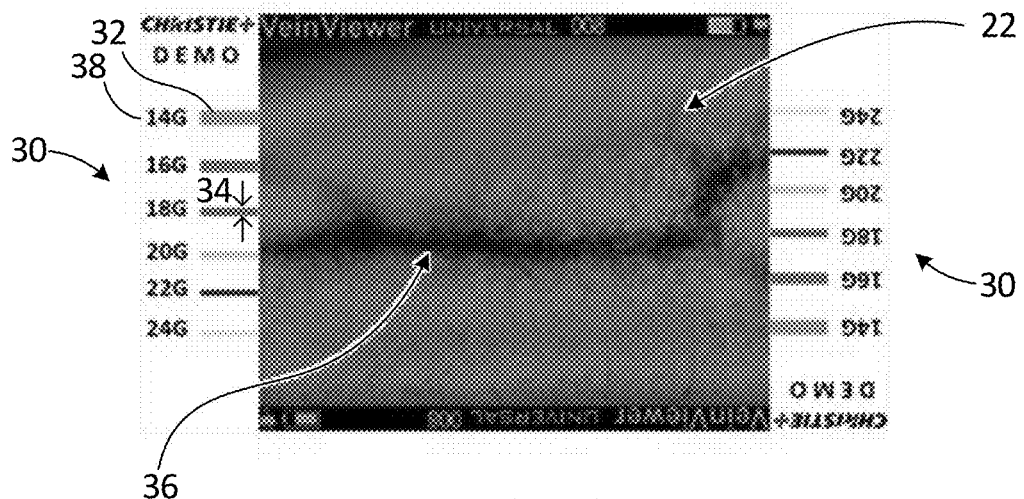
FIG. 2 is an example image of vasculature with a range of scale comparator objects.

As shown in FIG. 2, the processor 14 is configured to include in the output images displayed or projected, for example by the projector 16, the range of discrete scale comparator objects 30. Hence, the objects 30 are visible to the user of the device 10 as juxtaposed with imagery 22 of the vasculature, so that the user may make a direct visual comparison between any blood vessels visible and the objects 30, in order to ascertain a suitable size of peripheral IV catheter.

The range of discrete scale comparator objects 30 may be provided as a linear array, as depicted. Various arrangements are contemplated. In this example arrangement, two linear arrays are provided at opposites sides of the vascular imagery 22. That is, the two linear arrays are provided in border regions of the imagery, with the vascular imagery 22 being provided in the central region. The two linear arrays are reversed, so as to be visually consistent whether the user is looking from one side or the opposite side.

Further, the range of discrete scale comparator objects 30 may be kept static, that is unchanging over time, while the vascular imagery 22 is updated dynamically, for example while the device 10 is moved over the target tissue 20. As described elsewhere herein, the range of discrete scale comparator objects 30 may be configurable and adjustable and, hence, need not be completely static. Rather, the range of discrete scale comparator objects 30 is sufficiently static to allow a clinician to select a suitable catheter while the vascular imagery 22 is updated dynamically in real time or near real time.

Each discrete scale comparator object 30 may include a graphical representation 32 of a peripheral IV catheter of a particular diameter. The graphical representations 32 may be positioned to be contiguous with the vascular imagery 22, as depicted, so that the device 10 may be manipulated to position an image of a blood vessel adjacent a graphical representation 32 to facilitate accurate visual comparison. In the example depicted, the graphical representation 32 is a rectangle having a long side and a short side 34, the short side 34 matching the diameter of a peripheral IV catheter. The short side 34 is to be compared to blood vessels 36 in the vascular imagery 22, and so the short side 34 is aligned with the vascular imagery 22. The graphical representations 32 may be true size but need not be. Rather, the graphical representation 32 need only be the same scale as the imagery 22 of the vasculature.

In embodiments that use a projector 16, the common optical path 28 shared by the imager 12 and the projector 16, shown in FIG. 1, facilitates the apparent enlarging and shrinking of both the graphical representation 32 and the imagery 22 of the vasculature at the same rate, as the imaging device 10 is moved towards and away from the target tissue 20. As such, the range of discrete scale comparator objects 30 need only be provided at one scale and, in use, the objects 30 will be optically scaled at the same rate as the vascular imagery 22, so that the correct relative sizes of the objects 30 and the vascular imagery 22 will be maintained independently of the distance of the device 10 from the target tissue 20 over an acceptable range of distances.

The diameters of peripheral IV catheters may accord to standard gauge sizes. As such, the sizes of the graphical representations 32 may be provided in the same standard gauge sizes. For example, the short sides 34 of the rectangular graphical representations 32 may be 2.1 mm, 1.8 mm, 1.3 mm, 1.1 mm, 0.9 mm, and 0.7 mm in length to represent, respectively, standard gauge sizes of 14G, 16G, 18G, 20G, 22G, and 24G. This is merely one example standard and other standards may be used.

Figure 3:
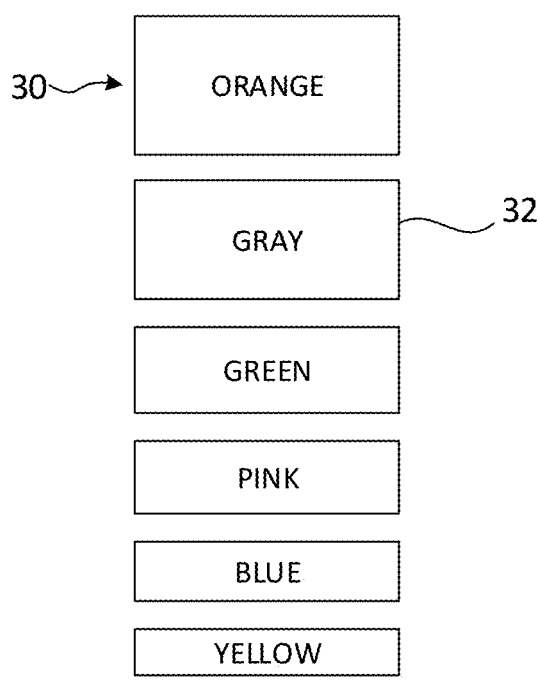
FIG. 3 is a schematic diagram of example colors of a range of scale comparator objects.

As shown in FIG. 3, each discrete scale comparator object 30 may be rendered in a true color that accords to a standard gauge size. For example, graphical representations 32 of standard gauge sizes of 14G, 16G, 18G, 20G, 22G, and 24G may be respectively colored orange, gray, green, pink, blue, and yellow. Hence, while the vascular imagery 22 is rendered in false color due to the fact that IR/NIR light is not normally visible to the human eye, the discrete scale comparator objects 30 are rendered in true color, so that the user may readily identify the peripheral IV catheter represented by a given discrete scale comparator object 30. Color information may additionally or alternatively be rendered as text.

Referring back to FIG. 2, the discrete scale comparator objects 30 may be labelled with numerical values 38 indicative of their different sizes. For example, text of a gauge size may be rendered at or near the respective graphical representation 32. This may assist the user to readily identify the peripheral IV catheter represented by a given discrete scale comparator object 30.

With reference back to FIG. 1, the device 10 may include a housing 40 that holds the imager 12. The housing 40 may further hold the other components of the device 10. For example, the device 10 may be a handheld device. The housing 40 may contain all the components of the device 10 or a subset of the components of the device 10 including the imager 12. For example, the processor 14 may be provided in a housing separate from a housing that contains the imager 12, where the components at the two housings communicate via a set of wires. The housing 40 may be shaped and sized to be manually oriented by the user.

Figure 4A:
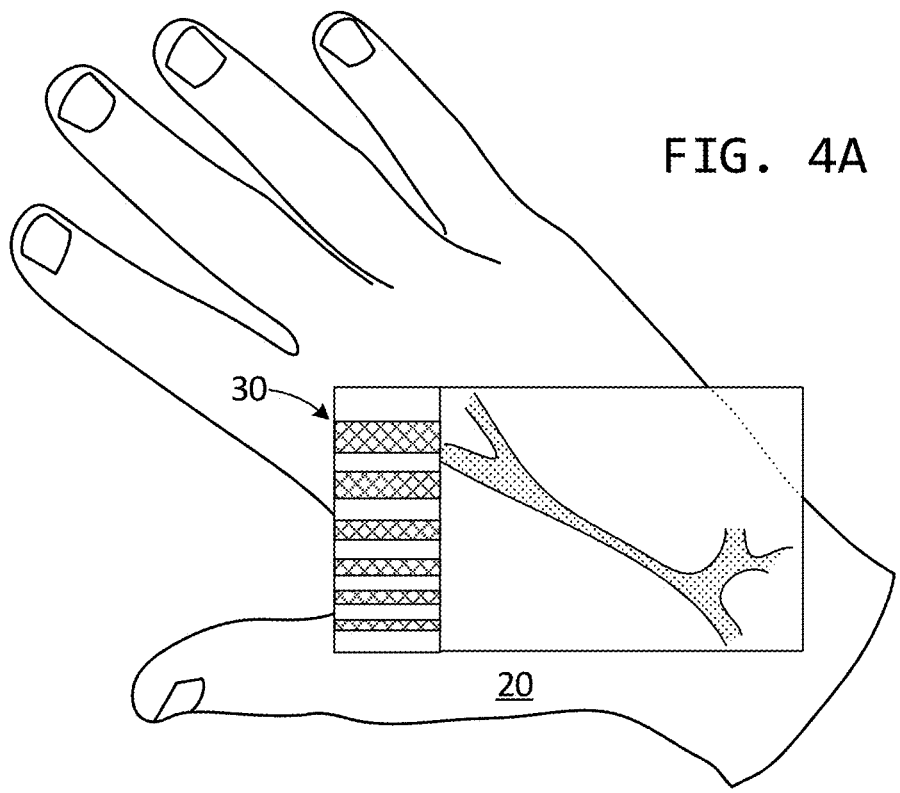
FIG. 4A is a schematic diagram of vascular imagery projected onto a subject's skin, where an imaging device is oriented such that a range of scale comparator objects is not aligned with a blood vessel.
Figure 4B:
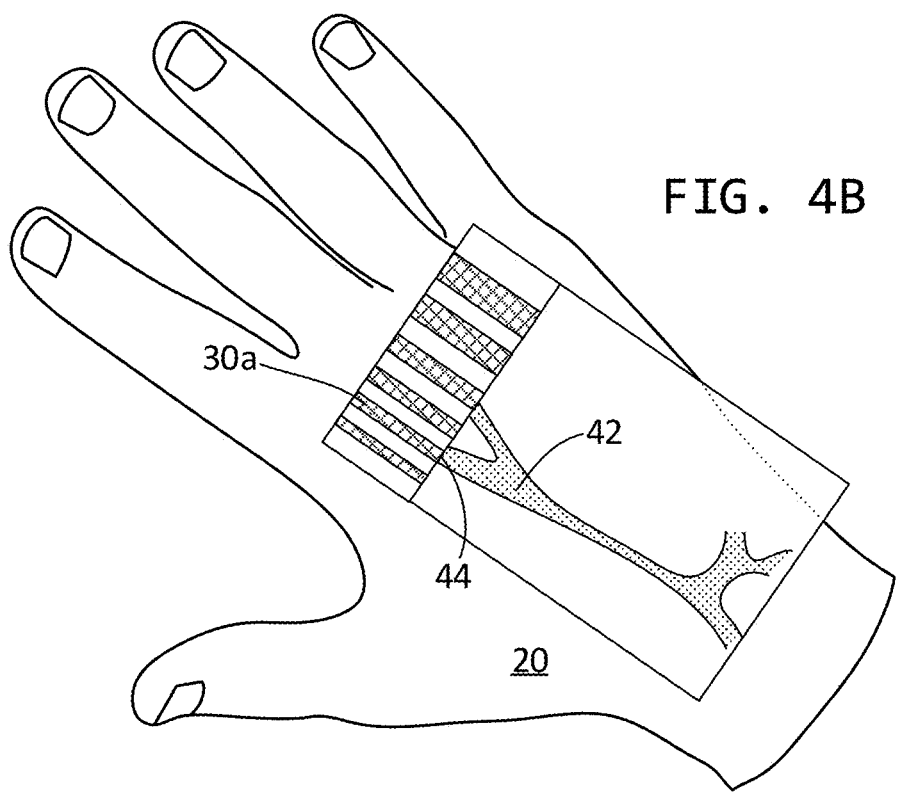
FIG. 4B is a schematic diagram of vascular imagery projected onto a subject's skin, where an imaging device is oriented such that a range of scale comparator objects is aligned with a blood vessel.

FIGS. 4A and 4B show output images projected onto target tissue. The housing 40 of the device may be orientable by the user to align the range of discrete scale comparator objects 30 with a blood vessel 42 displayed in the output images projected onto the target tissue 20. An initial orientation, as shown in FIG. 4A, may be manually changed by the user so as to align a particular discrete scale comparator object 30a with a particular blood vessel 42, as shown in FIG. 4B. The particular discrete scale comparator object 30a being contiguous, at 44, with the image of the blood vessel 42 allows the user to directly visually compare the particular discrete scale comparator object 30a with the particular blood vessel 42 to determine whether the peripheral IV catheter represented by the particular discrete scale comparator object 30a is suitable.

Further, in FIGS. 4A and 4B, the example range of discrete scale comparator objects 30 is rendered along one side of the vascular imagery.

FIGS. 5A-5E show various other example arrangements of range of discrete scale comparator objects.

Figure 5A:
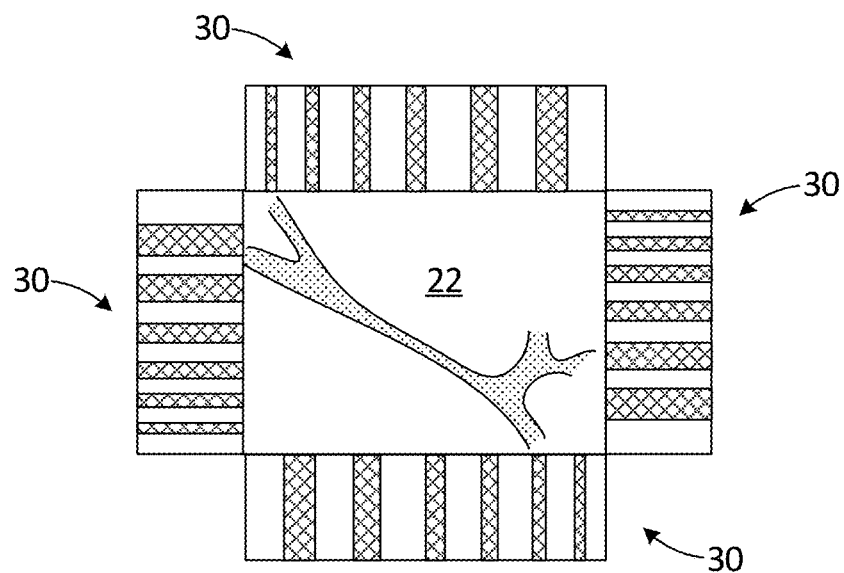
FIG. 5A is a schematic diagram of a plurality of ranges of scale comparator objects on multiple sides of central vascular imagery.

In the example shown in FIG. 5A, four range of discrete scale comparator objects 30 are used in a border region of a centrally located vascular imagery 22. The range of discrete scale comparator objects 30 may have opposing directions and may have different spacings of their individual objects.

Figure 5B:
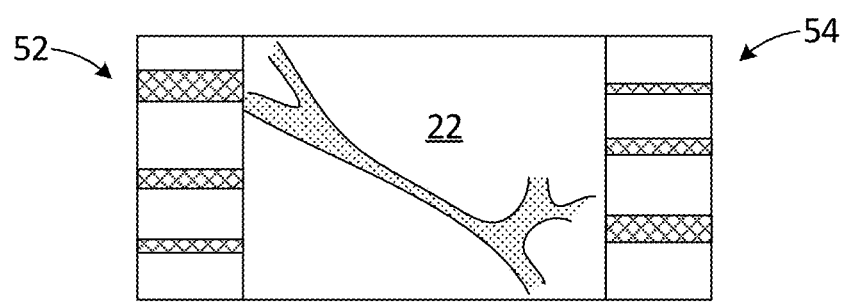
FIG. 5B is a schematic diagram of a plurality different subsets of scale comparator objects.

In the example shown in FIG. 5B, two different ranges of discrete scale comparator objects 50, 52 are display at different locations. Each range contains a different subset of individual objects that together form a full set.

Figure 5C:
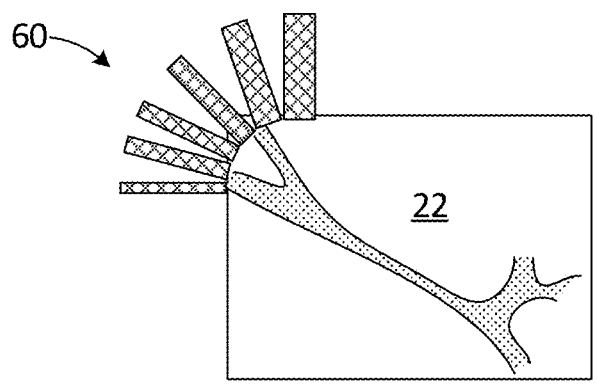
FIG. 5C is a schematic diagram of a range of scale comparator objects arranged in a curved array.

In the example shown in FIG. 5C, a range of discrete scale comparator objects 60 is arranged in a curved array, such as along a circle, circular segment, or arc.

Figure 5D:
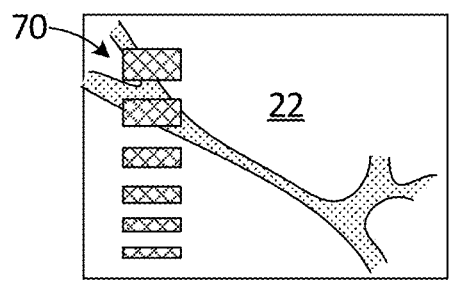
FIG. 5D is a schematic diagram of a range of scale comparator objects overlaying vascular imagery.

In the example shown in FIG. 5D, a range of discrete scale comparator objects 70 is overlaid onto vascular imagery 22. The objects may be rendered in outline or made partially transparent so that underlying vasculature remains visible.

Figure 5E:
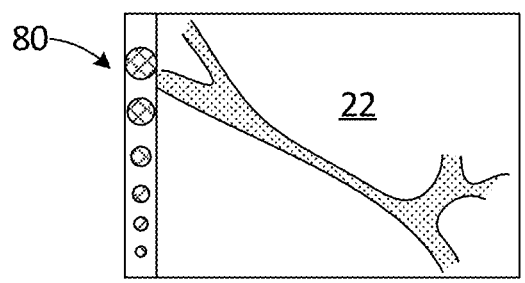
FIG. 5E is a schematic diagram of a range of scale comparator objects of circular shape.

In the example shown in FIG. 5E, a range of discrete scale comparator objects 70 may be formed of other shapes, such as circles, as depicted.

Figure 6:
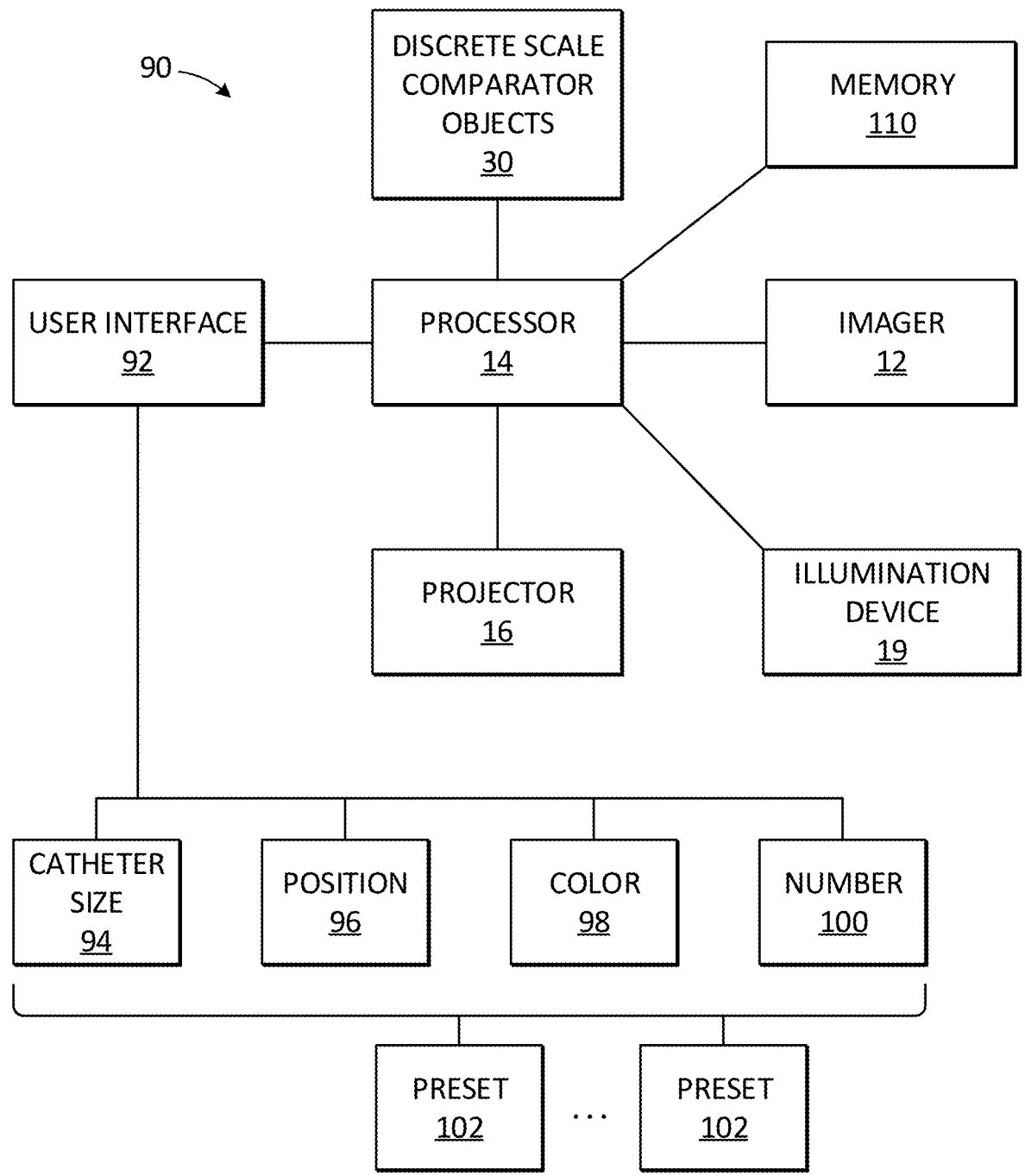
FIG. 6 is a diagram of a user interface to select a range of scale comparator objects.

FIG. 6 shows an imaging device 90 according to another embodiment of the present invention. The imaging device 90 is similar to the device 10 and only differences will be described in detail.

The device 90 may include a user interface 92 connected to the processor 14. The user interface 92 may include a touchscreen, keyboard, keypad, button, dial, or similar that allows for input from a user. Feedback to the user may be provided on a screen, touchscreen, or within the image projected by the projector 16. The user interface 92 may allow any aspect of a range of discrete scale comparator objects 30 to be selected by the user, such as catheter sizes to be represented 94 (e.g., specific individual sizes, standard sets of sizes, etc.), positioning of a range 96 (e.g., one side, two sides, all sides, left side, right side, etc.), colors shown 98, numerical values shown 100, and the like.

Additionally or alternatively, one or more preset 102 ranges of discrete scale comparator objects 30 may be configured at the factory or by the user. The user interface 92 may allow any preset 102 range to be selected for use.

The imaging device 90 may include memory 110, such as random-access memory (RAM), Electrically Erasable Programmable Read-Only Memory (EEPROM), flash memory, or similar connected to the processor 14. The processor 14 may be configured to store images in the memory 110. The processor 14 may be configured to store in the memory 110 images that include both vascular imagery and a range of discrete scale comparator objects. That is, stored images are captured images of vasculature that have been modified by the processor 14 to include a range of discrete scale comparator objects. This can facilitate the capture of evidence that a procedure has been performed as well as support the decision of a clinician in selecting a specific size of catheter. The device 90 may further include an input/output interface for obtaining images from the memory 110 for long-term storage at a computer, for example.

In view of the above, it should be apparent that a range of peripheral IV catheter selection information is provided to allow a clinician to efficiently exercise his/her professional judgement. Discrete scale comparator objects are provided in the same image as vasculature, so as to help a clinician visually asses a suitable catheter size. A physical object to provide scale is not needed. Further, the discrete scale comparator objects may be dynamic and/or configurable, so that a suitable range of comparator objects may be provided in real time or near real time to the clinician. The techniques described herein do not replace professional judgment by, for example, making recommendations, but rather support professional judgment in an automated and efficient manner.

It should be recognized that features and aspects of the various examples provided above can be combined into further examples that also fall within the scope of the present disclosure. In addition, the figures are not to scale and may have size and shape exaggerated for illustrative purposes.

What is claimed is:

1. A device comprising:
an imager to capture images of a living subject including a near-infrared image, an infrared image, or both;
an output device; and
a processor connected to the imager and the output device, the processor configured to:
generate output images of vasculature of the living subject from the images captured by the imager;
include in the output images a range of discrete scale comparator objects of different sizes; and
provide the output images to the output device for display to a user;
wherein the range of discrete scale comparator objects comprises objects of different colors that include standard colors of peripheral intravenous catheters.

2. The device of claim 1, wherein the range of discrete scale comparator objects represent different diameters of peripheral intravenous catheters.

3. The device of claim 2, wherein the range of discrete scale comparator objects represent standard gauge sizes of peripheral intravenous catheters.

4. The device of claim 1, wherein the different sizes of the range of discrete scale comparator objects are relative to an apparent size of the vasculature.

5. The device of claim 1, wherein the range of discrete scale comparator objects comprises a linear array of objects.

6. The device of claim 1, wherein the range of discrete scale comparator objects comprises a curved array of objects.

7. The device of claim 1, wherein the processor is configured to render the vasculature in false color, and wherein the processor is configured to render the standard colors in true color.

8. The device of claim 1, wherein the range of discrete scale comparator objects comprises labels of numerical values indicative of the different sizes.

9. The device of claim 8, wherein the numerical values include standard gauge sizes of peripheral intravenous catheters.

10. The device of claim 1, wherein the range of discrete scale comparator objects are included in a border of the output images, and wherein vasculature is to be included in a central region of the output images.

11. The device of claim 1, wherein the processor is configured to position the range of discrete scale comparator objects to be contiguous with imagery of vasculature included in a central region of the output images.

12. The device of claim 1, wherein the processor is configured to dynamically generate the output images of vasculature of the living subject from the images captured by the imager, and wherein the range of discrete scale comparator objects is static.

13. The device of claim 1, wherein the range of discrete scale comparator objects is selectable from a plurality of different ranges of discrete scale comparator objects.

14. The device of claim 1, further comprising a housing to hold the imager, wherein the housing is orientable by the user to align the range of discrete scale comparator objects with a blood vessel displayed in the output images.

15. The device of claim 1, wherein the output device comprises a projector to project the output images onto the skin of the living subject, wherein the projector and imager share a common optical path.

16. The device of claim 15, wherein the common optical path provides consistent relative apparent sizes of the discrete scale comparator objects and the vasculature independent of a distance of the imager from the living subject over an acceptable range of distances.

17. A method to assist insertion of a catheter, the method comprising:
capturing images of a living subject including a near-infrared image, an infrared image, or both using an imager;
generating output images of vasculature of the living subject from the images captured by the imager;
including in the output images a range of discrete scale comparator objects of different sizes; and
providing the output images to an output device for display to a user; and
wherein the range of discrete scale comparator objects comprises objects of different colors that include standard colors of peripheral Intravenous catheters.

18. A device comprising:
an imager to capture images of a living subject including a near-infrared image, an infrared image, or both;
an output device; and
a processor connected to the imager and the output device, the processor configured to:
dynamically generate output images of vasculature of the living subject from the images captured by the imager, wherein the vasculature is rendered in false color;
include in the output images a relatively static range of discrete scale comparator objects of different sizes that are relative to an apparent size of the vasculature, wherein the range of discrete scale comparator objects represents standard gauge sizes and standard colors of peripheral intravenous catheters;
render in the output images the standard colors of the peripheral intravenous catheters in true color; and
provide the output images to the output device for display to a user.

19. A device comprising:
an imager to capture images of a living subject including a near-infrared image, an infrared image, or both;
an output device; and
a processor connected to the imager and the output device, the processor configured to:
generate output images of vasculature of the living subject from the images captured by the imager;
include in the output images a range of discrete scale comparator objects of different sizes; and
provide the output images to the output device for display to a user;
wherein the output device comprises a projector to project the output images onto the skin of the living subject, and wherein the projector and imager share a common optical path.

20. The device of claim 19, wherein the common optical path provides consistent relative apparent sizes of the discrete scale comparator objects and the vasculature independent of a distance of the imager from the living subject over an acceptable range of distances.

* * * * *